Figure 1:
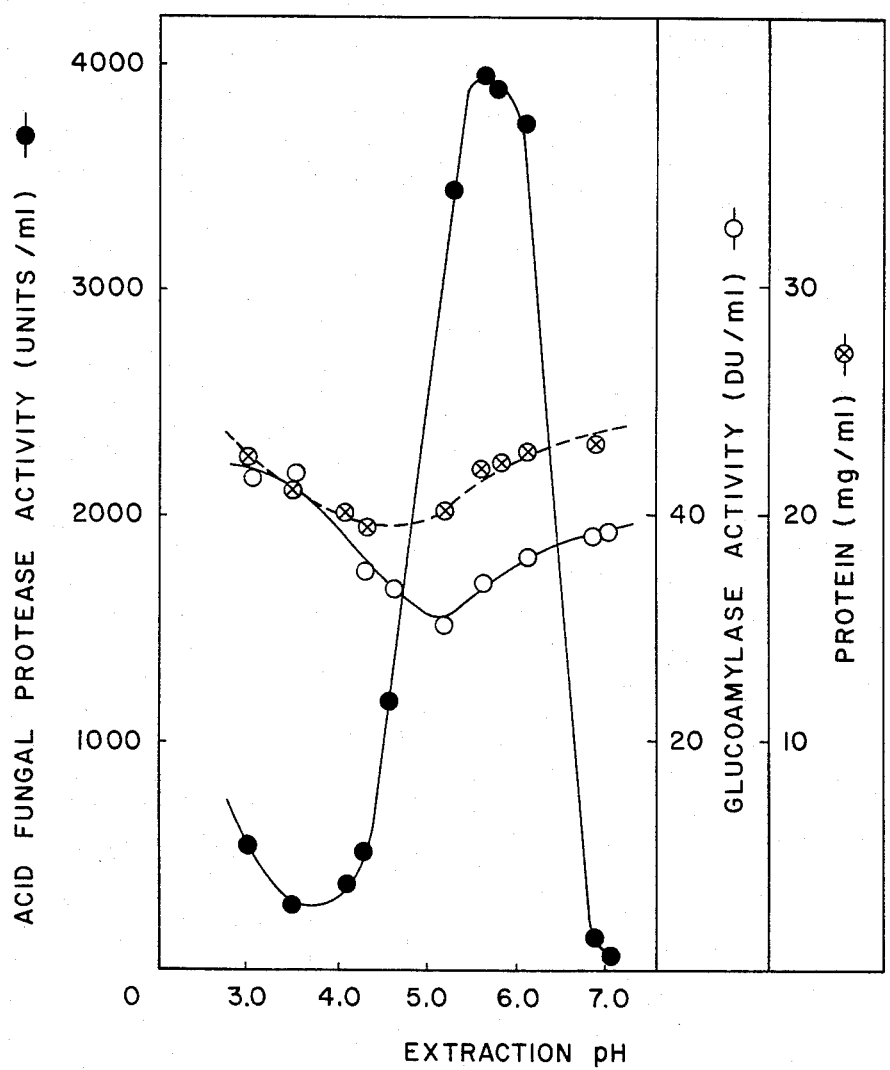

United States Patent [19]

Shetty et al.

[11] Patent Number: 4,532,213

[45] Date of Patent: Jul. 30, 1985

[54] RECOVERY OF ACID FUNGAL PROTEASE

[75] Inventors: Jayarama K. Shetty; James J. Marshall, both of Elkhart, Ind.

[73] Assignee: Miles Laboratories, Inc., Elkhart, Ind.

[21] Appl. No.: 559,341

[22] Filed: Dec. 8, 1983

[51] Int. Cl.$^3$ .......................... C12N 9/34; C12N 9/58; C12N 9/62

[52] U.S. Cl. ..................... 435/225; 435/223; 435/205; 435/814

[58] Field of Search .................. 435/205, 223, 225

[56] References Cited

U.S. PATENT DOCUMENTS 3,892,629  7/1975  Smith et al. ........................ 435/254

OTHER PUBLICATIONS

Tomonaga, J. Gen. Appl. Microbiol., 12, 267, (1966).
Tomonaga et al., J. Gen. Appl. Microbiol., 10, 373 (1964).
Ichishima et al., Biochem. Biophys. Acta, 99, 360, (1965).

*Primary Examiner*—Lionel M. Shapiro
*Attorney, Agent, or Firm*—Jerome L. Jeffers

[57] ABSTRACT

Glucoamylase and acid fungal protease co-produced by the fermentation of fungal species capable of producing these enzymes are separated by carrying out the fermentation at a pH at which the protease associates itself with the fungal mycelium and removing the mycelium from the fermentation broth. The mycelium is then resuspended in an aqueous medium and the pH adjusted to cause the dissociation of the protease and mycelium with subsequent recovery of the protease from the aqueous medium.

7 Claims, 2 Drawing Figures

RECOVERY OF ACID FUNGAL PROTEASE

BACKGROUND OF THE INVENTION

Fungal glucoamylase preparations, particularly those derived from members of the Aspergillus and the Rhizopus genera are known to convert starchy materials to substantial amounts of dextrose. In addition, certain fungi capable of producing glucoamylase under suitable fermentation conditions also produce acid fungal protease. The acid fungal protease co-produced is potentially useful in the food, brewing and photographic industries. Thus, this protease can be used in the preparation of protein hydrolysates at low pH values (soy sauce), preparation of orange juice concentrate (peeling the skin), prevention of chill haze in beer (as a potential replacement for papain) and as a digestive aid in animal feed (chicks, piglets, etc.).

Acid fungal proteases have been isolated from the culture filtrates of *Aspergillus niger, Aspergillus saitoi, Aspergillus oryzae* and *Aspergillus niger* var. macrosphorus and Rhizopus species.

It is, of course, desirable to separate the glucoamylase from the acid fungal protease produced during the fermentation of these organisms both to purify the glucoamylase and to provide a useful byproduct of the fermentation.

In the prior art, for example, Tomonaga reports in *J. Gen. Appl. Microbiol.*, 12, 267 (1966) that acid protease is precipitated using certain salts and recovered by ion-exchange chromatography. More specifically, the enzyme was fractionated using DEAE-cellulose and SE-sephadex column chromatography at pH 4.1 using the procedures disclosed by Tomonaga, et at, *J. Gen. Appl. Microbiol*, 10, 373 (1964) and Ichishima, et al, *Biochem. Biophys. Acta*, 99, 360 (1965).

We have discovered that at a certain pH range, the acid fungal protease is associated with the fungal mycelium, i.e. biomass, in the fermentation broth and it is an object of this invention to provide a simple method for the recovery in good yields of acid fungal protease from the fungal mycelium.

SUMMARY OF THE INVENTION

The present invention is a method for the recovery of acid fungal protease produced during the fermentation in an aqueous nutrient medium of a fungus capable of producing extracellular glucoamylase and acid fungal protease. This method involves the steps of:

(a) introducing the fungus to the aqueous media and allowing it to grow at a pH of from about 2.0 to 4.8 and under conditions which result in the production of extracellular glucoamylase and acid fungal protease which acid fungal protease is associated with fungal mycelium produced during the fermentation;

(b) separating the fungal mycelium and acid fungal protease associated therewith from the aqueous medium by liquid/solid separation techniques;

(c) resuspending the fungal mycelia in an aqueous medium and adjusting the pH to a level of from about 5.0 to 6.5 to facilitate the dissociation of the fungal mycelium and the acid fungal protease associated therewith thereby causing the acid fungal protease to enter the aqueous medium; and (d) separating the fungal mycelium from the aqueous medium to thereby provide an aqueous medium containing recoverable quantities of acid fungal protease.

DESCRIPTION OF THE INVENTION

The present invention is predicated on the discovery that in the type of fermentation previously described, the acid fungal protease is associated with the fungal mycelium when the pH of the fermentation broth is maintained at a level of from about 2.0 to 4.8 and preferably from about 3.8 to 4.2. Acid fungal protease is an extracellular enzyme and may be associated with fungal mycelium through noncovalent interactions, i.e. electrostatic, hydrophobic or hydrogen bonding under the conditions of fermentation. By carrying out the fermentation in the normal manner which results in the production of glucoamylase and acid fungal protease, in a medium with a pH of 4.8 or less, the protease remains associated with fungal mycelium thereby creating a liquid phase containing glucoamylase and a solid phase containing acid fungal protease. These phases can be separated by conventional liquid/solid separation techniques such as centrifugation with decantation or by filtration.

Upon separation of the liquid (glucoamylase-containing) phase and the solid (acid fungal protease-containing) phase, the glucoamylase is recovered by conventional means. We have discovered that the fungal acid protease can be separated from the fungal mycelium by resuspending the mycelium in an aqueous medium and adjusting the pH of this suspension to a level of from 5.0 to 6.5 and preferably to a level of 5.6 to 5.8. Separating the liquid medium containing the enzyme from the fungal mycelium by liquid/solid separation techniques provides a liquid phase containing recoverable quantities of acid fungal protease which can be recovered by conventional means The method of practicing this invention is further illustrated by the following examples.

EXAMPLE I

Effect of pH on the release of acid protease and glucoamylase from fungal mycelia An organism from a fungal strain of the *Aspergillus niger* group was cultivated in an aqueous nutrient medium containing corn mash, vitamins, minerals and proteins for a period of 180 hours at a pH of 3–4 and a temperature of 30°–34° C. Several aliquots (50 ml each) were removed and each was adjusted to a different pH; i.e., 2.0, 2.5, 3.0, 3.5, 4.0, 4.25, 4.3, 4.75, 5, 6, 6.5, 7.0 and 8.0, using 2N NaOH and 2N HCl. The suspension was continuously stirred for 45 minutes at 25° C. (20° C.–30° C.) and centrifuged at 15,000 rpm for 45 minutes at 5° C. The supernatant solution was decanted and further clarified by filtration. The acid protease activity, glucoamylase activity and total protein measurements were conducted as follows:

Glucoamylase:

Glucoamylase activity was determined by following the procedure described in U.S. Pat. No. 3,249,514. One unit of enzyme activity (DU) is that amount which will liberate one gram of reducing sugar as glucose per hour under the conditions of the assay.

Acid Protease:

This activity was measured using Azocoll as substrate. Azocoll (50 mg) was incubated with acid protease in 5 ml of sodium acetate buffer, pH 3.6 (0.1M) at 50° C. for 60 minutes whereupon the enzyme reaction was terminated by filtering the reaction mixture. The acid protease activity was then determined by measuring the optical density of the colored solution at 520 nm. A unit of acid protease was defined as the amount of the enzyme required to increase the optical density at 520 nm by 0.10 unit under the specified conditions of the assay.

Protein:

A protein-dye binding method was followed to quantitate the proteins, Bradford, *Anal. Biochem.*, 72, 248 (1976). Protein solution (0.1 ml) was pipetted into a test tube and 5 ml of the protein-dye reagent added thereto followed by vortex mixing of the contents. The absorbance at 595 nm was measured after 5 minutes against a reagent blank prepared from 0.1 ml of water and 5 ml of protein-dye reagent. The amount of the protein was then determined from a standard curve prepared from bovine gamma-globulin.

The results of these determinations are graphically summarized in FIG. 1. Referring to FIG. 1, it can be determined that a marked increase in the soluble acid protease activity was observed in the fractions extracted between pH 4.8 and 6.5. In other words, most of the acid protease was found to be associated with fungal mycelium between pH 3.2 and 4.2. It is also interesting to note that extraction of the acid protease from fungal mycelium above pH 7.0 caused the irreversible inactivation of the acid protease. On the other hand, the solubility of the total protein was not significantly effected by changing the pH of the extraction. A slight decrease in the release of glucoamylase from the mycelium was observed between pH 4.8 and 5.5 compared to the extraction of glucoamylase at pH 3.0 and 7.0. However, the protein extracted from the broth below pH 4.2 exhibited higher glucoamylase activities compared with the protein extracted from the broth above pH 5.5. The total amount of protein extracted under these two conditions was the same and hence the observed differences in the glucoamylase activity may possibly be due to the partial denaturation of glucoamylase above pH 5.5.

More than 90% of the total acid protease was associated with fungal mycelia between pH 3.2 and 4.2. Extraction of glucoamylase was decreased between pH 4.8 and 5.5. While the present invention is not predicated on any particular theory or mechanism of action, it is believed that since glucoamylase is a glycoprotein, the significant increase in the hydrogen bonding between the hydroxyl groups of the carbohydrate portion of the glucoamylase and water may greatly decrease the adsorption of glucoamylase to mycelium at the isoelectric pH. Thus, the separation of these enzymes (glucoamylase and acid fungal protease) is shown to be pH dependent.

EXAMPLE II

Figure 2:
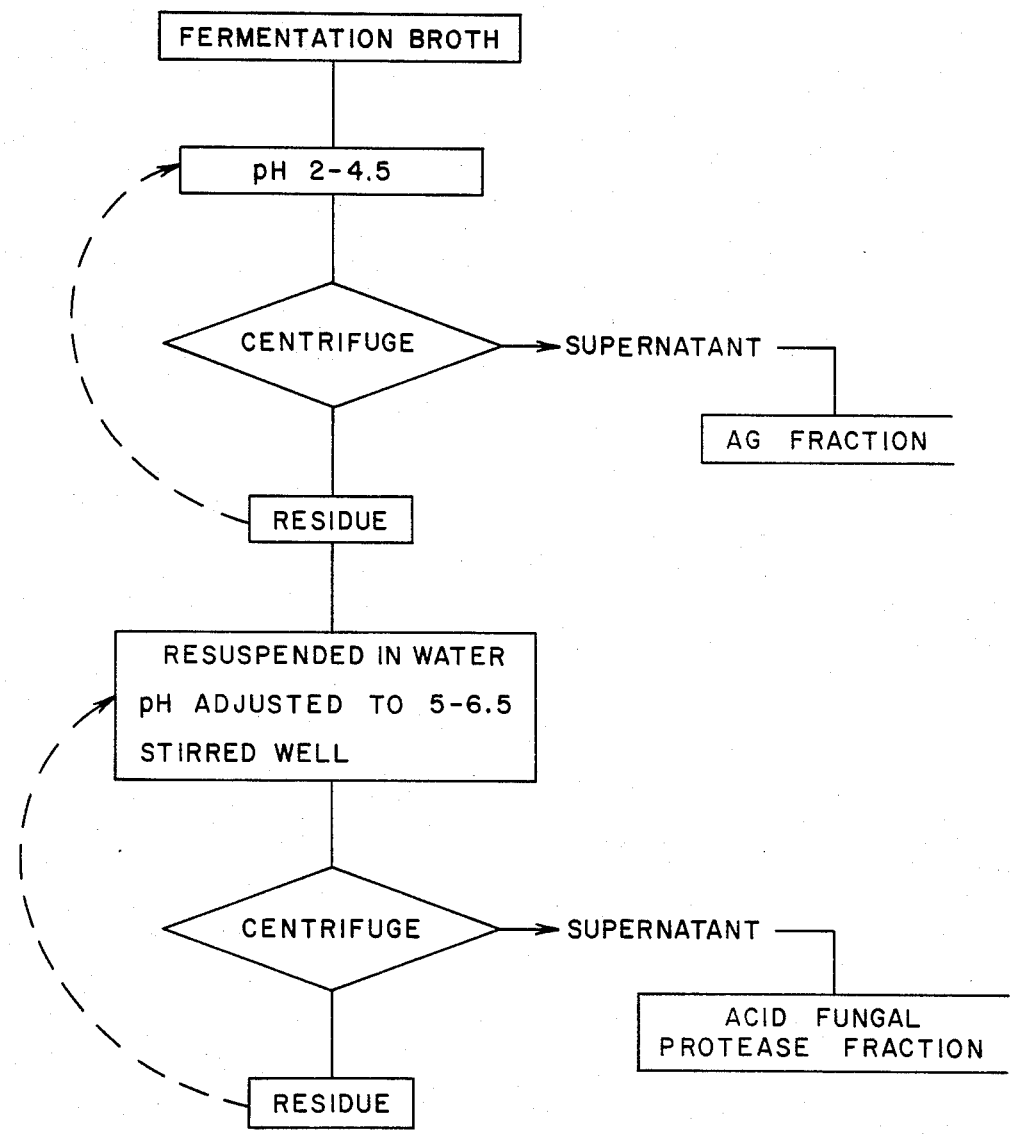

As described in detail above, a process suitable for separation and purification of acid fungal protease during the commercial production of glucoamylase has been developed and is schematically illustrated by FIG. 2. This separation was accomplished as follows:

A glucoamylase fermentation broth (500 ml) was adjusted to pH 4.0 and centrifuged at 7,000 rpm for 20 minutes. The supernatant solution containing glucoamylase was separated and the residue (mycelial fraction containing acid fungal protease) was resuspended in 500 milliliters of water with the suspension being stirred well for uniform mixing. The pH of the suspension was adjusted to 4.0 and the residue was separated by centrifugation. The clear supernatant solution was then combined with the glucoamylase fraction. Repeated washing of the mycelial cake at pH 4.0 with water causes the separation of glucoamylase from the fungal mycelial fraction containing acid protease. The washed fungal mycelial cake containing acid fungal protease was resuspended in 500 milliliters of water and the pH was adjusted to 5.6–5.8 using 3N NaOH and stirred for another 45 minutes. The suspension was centrifuged at 7,000 rpm for 30 minutes and the acid protease fraction (supernatant I) was separated. Extraction of the residue with water at pH 5.6–5.8 was repeated once again (supernatant II). Determination of acid fungal protease activity in supernatant I and supernatant II indicated that more than 80% of the total acid fungal protease was recovered in the first extraction. The total acid fungal protease recovered from 500 ml of glucoamylase fermentation broth contained 96,700 acid protease units.

What is claimed is:

1. A method for the recovery of acid fungal protease produced during the fermentation in an aqueous nutrient medium of a fungus capable of producing extracellular glucoamylase and acid fungal protease which method comprises the steps of:

(a) introducing the fungus to the aqueous media and allowing it to grow at a pH of from about 2.0 to 4.8 under conditions which result in the production of extracellular glucoamylase and acid fungal protease which acid fungal protease is associated with fungal mycelium produced during the fermentation;

(b) separating the fungal mycelium and acid fungal protease associated therewith from the aqueous medium by liquid/solid separating techniques;

(c) resuspending the fungal mycelium in an aqueous medium and adjusting the pH to a level of from about 5.0 to 6.5 to facilitate the dissociation of the fungal mycelium and the acid fungal protease associated therewith thereby causing the acid fungal protease to enter the aqueous medium; and (d) separating the fungal mycelium from the aqueous medium to thereby provide an aqueous medium containing recoverable quantities of acid fungal protease.

2. The method of claim 1 wherein the species of fungi is *Aspergillus niger*.

3. The method of claim 1 where the separation of fungal mycelia from the aqueous nutrient medium is carried out at a pH of 3.8 to 4.2.

4. The method of claim 2 where the separation of fungal mycelia from the aqueous nutrient medium is carried out at a pH of 3.8 to 4.2.

5. The method of claim 1 where the pH is adjusted to a level of from 5.6 to 5.8 after resuspending the fungal mycelia.

6. The method of claim 2 where the pH is adjusted to a level of from 5.6 to 5.8 after resuspending the fungal mycelia.

7. The method of claim 3 where the pH is adjusted to a level of from 5.6 to 5.8 after resuspending the fungal mycelia.

* * * * *